(12) United States Patent
Yoon et al.

(10) Patent No.: US 12,097,467 B2
(45) Date of Patent: Sep. 24, 2024

(54) SYSTEMS AND TECHNIQUES FOR CLEANING PRESSURE MEMBRANE SYSTEMS USING A WATER-IN-AIR CLEANING STREAM

(71) Applicant: Ecolab USA Inc., Saint Paul, MN (US)

(72) Inventors: Seong-Hoon Yoon, Naperville, IL (US); Hui Li, Bolingbrook, IL (US); Craig Myers, Lisle, IL (US); Daniel Meier, Naperville, IL (US); Donald Johnson, Batavia, IL (US)

(73) Assignee: Ecolab USA Inc., Saint Paul, MN (US)

( * ) Notice: Subject to any disclaimer, the term of this patent is extended or adjusted under 35 U.S.C. 154(b) by 287 days.

(21) Appl. No.: 17/576,984

(22) Filed: Jan. 16, 2022

(65) Prior Publication Data
US 2022/0226782 A1 Jul. 21, 2022

Related U.S. Application Data

(60) Provisional application No. 63/138,770, filed on Jan. 18, 2021.

(51) Int. Cl.
*B01D 65/02* (2006.01)
*C02F 1/44* (2023.01)
(Continued)

(52) U.S. Cl.
CPC ............... *B01D 65/02* (2013.01); *C02F 1/44* (2013.01); *G01N 21/78* (2013.01); *G01N 33/18* (2013.01);
(Continued)

(58) Field of Classification Search
CPC .... B01D 65/02; B01D 65/08; B01D 2321/18; B01D 2321/185; C02F 2103/023
See application file for complete search history.

(56) References Cited

U.S. PATENT DOCUMENTS

| 4,756,875 A | 7/1988 | Tajima et al. |
| 5,783,083 A | 7/1998 | Henshaw et al. |

(Continued)

FOREIGN PATENT DOCUMENTS

| CN | 105923796 A | * | 9/2016 |
| EP | 1599276 B1 | | 5/2008 |

(Continued)

OTHER PUBLICATIONS

Zhang, Wei, Han Zhang, and Anhong Zhou. "Smartphone colorimetric detection of calcium and magnesium in water samples using a flow injection system." Microchemical Journal 147 (2019): 215-223. (Year: 2019).*

(Continued)

*Primary Examiner* — Bradley R Spies
(74) *Attorney, Agent, or Firm* — Fredrikson & Byron, P.A.

(57) ABSTRACT

Membrane filtration systems can be used to purify liquid streams for downstream use. In practice, foulant can build-up on the surface of a membrane within a filtration system over time. The effectiveness of the filtration system will deteriorate if the fouling is not properly controlled. In some examples, a method of controlling membrane fouling in a pressurized membrane system involves supplying a feed stream that is predominately air mixed with water to the membrane. In other words, the feed stream a greater volume of air than water, even though it is the water being processed by the membrane. Supplying the pressurized membrane system with a feed stream that contains a greater volume of air than water can yield significantly better performance than supplying the membrane with a feed stream that contains a greater volume of water than air.

20 Claims, 3 Drawing Sheets

(51) Int. Cl.
*C02F 103/02* (2006.01)
*G01N 21/78* (2006.01)
*G01N 33/18* (2006.01)

(52) U.S. Cl.
CPC ...... *B01D 2321/10* (2013.01); *B01D 2321/16* (2013.01); *B01D 2321/185* (2013.01); *C02F 2103/023* (2013.01); *C02F 2209/055* (2013.01); *C02F 2209/38* (2013.01); *C02F 2209/40* (2013.01); *C02F 2303/16* (2013.01)

(56) References Cited

U.S. PATENT DOCUMENTS

| | | | |
|---|---|---|---|
| 6,193,890 | B1 | 2/2001 | Pedersen et al. |
| 6,245,239 | B1 | 6/2001 | Cote et al. |
| 6,550,747 | B2 | 4/2003 | Rabie et al. |
| 6,863,817 | B2 | 3/2005 | Liu et al. |
| 7,459,083 | B1 | 12/2008 | Hong et al. |
| 7,820,050 | B2 | 10/2010 | Cote et al. |
| 8,758,622 | B2 | 6/2014 | Muller |
| 9,206,057 | B2 | 12/2015 | Zha et al. |
| 9,783,434 | B2 | 10/2017 | Ginzburg et al. |
| 9,815,027 | B2 | 11/2017 | Phelps et al. |
| 9,862,628 | B2 | 1/2018 | Livingston et al. |
| 9,956,530 | B2 | 5/2018 | Johnson et al. |
| 2003/0183575 | A1* | 10/2003 | Zeiher ............ B01D 61/54 210/639 |
| 2006/0091074 | A1 | 5/2006 | Pedersen et al. |
| 2006/0273007 | A1 | 12/2006 | Zha et al. |
| 2007/0084795 | A1 | 4/2007 | Jordan |
| 2021/0130196 | A1 | 5/2021 | Yoon et al. |
| 2021/0322928 | A1 | 10/2021 | Yoon et al. |
| 2022/0203304 | A1* | 6/2022 | Färber ............ C02F 1/444 |

FOREIGN PATENT DOCUMENTS

| | | | |
|---|---|---|---|
| WO | 2005042132 | A1 | 5/2005 |
| WO | 2007043879 | A1 | 4/2007 |
| WO | WO-2020201424 | A1 * | 10/2020 ......... B01D 61/145 |

OTHER PUBLICATIONS

Liu J—CN-105923796—A machine translation—Sep. 7, 2016 (Year: 2016).*
"Membrane Filtration," Minnesota Rural Water Association, MN Water Works Manual, Chapter 19, Retrieved from https://www.mrwa.com/WaterWorksMnl/Chapter%2019%20Membrane%20Filtration.pdf on Jun. 8, 2020, 12 pages.
"Microza—Highly Efficient, Precise Filtration, Durable Module. Deployed in various liquid separation, filtration, and purification processes," Asahi Kasei, Retrieved from https://www.asahi-kasei.co.jp/membrane/microza/en/about_microza.html on Sep. 19, 2019, 2 pages.
"Wastewater Management Fact Sheet: Membrane Bioreactors," United States Environmental Protection Agency, Sep. 2007, 9 pages.
Akhondi et al., "The Performance and Fouling Control of Submerged Hollow Fiber (HF) Systems: A Review," Applied Sciences, vol. 7, 2017, 39 pages.
Cui et al., "The use of gas bubbling to enhance membrane processes," Journal of Membrane Science, vol. 221, 2003, pp. 1-35.
Hui et al., "Optimal Design of Aeration System in Submerged Membrane Bioreactor," Journal of Tianjin University, vol. 40, No. 8, Aug. 2007, 5 pages, English Abstract submitted.
Lucas, "Low Pressure Membrane Filtration System Operations," MISCO Water, New Mexico PWO Seminar, Retrieved from https://www.rmwea.org/docs/PWO_Seminar_Presentation_6-7-18_Nick_Lucas.pdf on Jun. 8, 2020, dated Jun. 7, 2018, 32 pages.
International Patent Application No. PCT/US2022/012649, International Search Report and Written Opinion mailed Apr. 26, 2022, 20 pages.
Cabassud et al., "How slug flow can improve ultrafiltration flux in organic hollow fibres", Journal of Membrane Science, vol. 128, No. 1, May 28, 1997, pp. 93-101.
Mercier et al., "How slug flow can enhance the ultrafiltration flux in mineral tubular membranes", Journal of Membrane Science, vol. 128, No. 1, May 1, 1997, pp. 103-113.
Um et al., "Flux enhancement with gas injection in crossflow ultrafiltration of oily wastewater", Water Research, vol. 35, No. 17, Dec. 1, 2001, pp. 4095-4101.

* cited by examiner

SYSTEMS AND TECHNIQUES FOR CLEANING PRESSURE MEMBRANE SYSTEMS USING A WATER-IN-AIR CLEANING STREAM

RELATED MATTERS

This application claims the benefit of U.S. Provisional Patent Application No. 63/138,770, filed Jan. 18, 2021, the entire contents of which are incorporated herein by reference.

TECHNICAL FIELD

This disclosure relates to systems and techniques for cleaning pressure membrane systems, particularly pressure membrane systems used upstream of a water analysis device, using a water-in-air cleaning stream.

BACKGROUND

Membrane separation is a technology that selectively separates materials via pores and/or minute gaps in the molecular arrangement of a continuous membrane structure. Membrane separations can be classified by pore size and by the separation driving force. Example membrane separation techniques include microfiltration (MF), ultrafiltration (UF), ion-exchange (IE), and reverse osmosis (RO). For example, reverse osmosis is widely used in water purification processes to remove ions, bacteria, and other molecules and larger particles from the water. In a reverse osmosis process, an applied pressure is used to overcome an osmotic pressure across the membrane, allowing substantially pure solvent (e.g., water) to pass through the membrane while a residual solute is retained on the pressurized side of the membrane.

During operation of a membrane separation system, clean water can pass through the membrane surface while contaminants can sit on the surface of the membrane. Contaminants can build up over time, even if there is a crossflow across the surface of the membrane, due to a phenomenon called concentration polarization. The length of time the membrane can stay in service before replacement or shutdown for cleaning can depend on how well concentration polarization and subsequent filter fouling are controlled.

SUMMARY

In general, this disclosure is directed to systems and technique for controlling fouling in closed membrane separation systems using a water-in-air stream in which the feed stream supplied to the separation system contains a greater volume of air than water. Introducing air into the feed stream can provide a scouring effect on the surface of the membrane that helps prevent deposition of foulant and/or helps remove built-up foulant. It has been found that using a feed stream where the amount of air exceeds the amount of water results in unexpectedly better fouling control and membrane performance improvements than when using a comparable feed stream where the amount of water exceeds the amount of air in the stream.

Although the systems and techniques of the disclosure can be used in a variety of different applications, in some implementations, the systems and techniques are utilized to control fouling in a pre-filtration system upstream of an automated water analysis system. An automated water analysis system may be used to analyze one or more chemical species in a variety of different industrial waters. This can provide information concerning the concentration of the one or more chemical species of interest in the industrial water, allowing the operator to take appropriate corrective action based on the measured concentration. For example, the operator may adjust an operating parameter of the industrial water system and/or control the introduction of a chemical additive to the industrial water system that interacts with the chemical species of interest.

When an automated water analysis system is implemented as an online tool, the system may receive a sample of water from the industrial water system, perform a prefiltration on the water sample, and then analyze the resulting filtered sample for the one or more chemical species of interest. In some implementations, the automated water analysis system may control addition of an optical indicator to the filtered water sample and perform a colorimetric optical analysis to determine the concentration of the one or more chemical species of interest. Performing prefiltration on the water sample can remove comparatively large size particulates and contaminants, which may otherwise interfere with the optical analysis performed on the water sample.

In practice, an operator may install an automated water analysis system with the intent that the water analysis system operates continuously for an extended period of time without requiring user intervention. If the prefiltration system of the water analysis system becomes prematurely fouled, this can require accelerated user intervention for maintenance on the water analysis system.

In accordance with some examples of the present disclosure, a membrane filtration system utilizing a feed stream that contains a greater amount of air than water is utilized as a prefiltration step for an automated water analysis system. This can generate a filtered water stream for downstream analysis, such as the determination of the concentration of one or more chemical species of interest in the water stream. By distributing the water stream to be filtered in the membrane system in an airstream of greater volume, fouling on the membrane element may be reduced or eliminated as compared to when the water stream is processed directly on the membrane and/or processed with a lesser volume of air. This can extend the service life and duration between which user maintenance is needed on the membrane filtration system.

While the systems and techniques of the disclosure can be beneficially used to support extended operation of an automated water analysis system, the disclosure is not limited to the specific application. As another example, the systems and techniques can be used in larger scale water purification processes in which a contaminated water stream is processed by one or more membrane filtration elements to produce a clean water stream for downstream use.

In one example, a method of controlling pre-filtration fouling in an automated water analysis system is described. The method includes generating a feed stream by combining a flow rate of air with a flow rate of water, where a ratio of the flow rate of air divided by the flow rate of water is greater than 1. The method also includes contacting a membrane with the feed stream inside of a housing, thereby generating a permeate stream and a concentrate stream, wherein the housing pressure isolates the membrane from an ambient environment. In addition, the method involves analyzing the permeate stream to determine a concentration of at least one chemical species in the permeate stream.

In another example, a method of controlling membrane fouling comprising is described that includes generating a feed stream by combining a flow rate of air with a flow rate of water, wherein a ratio of the flow rate of air divided by the flow rate of water is greater than 1. The method also includes contacting a membrane with the feed stream inside of a housing, thereby generating a permeate stream and a concentrate stream, where the housing pressure isolates the membrane from an ambient environment.

In an additional example, a system is described that includes a membrane, a water metering device, an air metering device, an analyzer, and a controller. The membrane is positioned in a housing that pressure isolates the membrane from an ambient environment, with the membrane being configured to separate a feed stream into a permeate stream and a concentrate stream. The water metering device is configured to provide a flow rate of water. The air metering device is configured to provide a flow rate of air that combines with the flow rate of water to generate the feed stream supplied to the housing. The analyzer is positioned to measure a concentration of at least one chemical species in the permeate stream. The controller is communicatively coupled to the water metering device, the air metering device, and the analyzer. The example specifies that the controller is configured to control the water metering device and the air metering device to generate the feed stream with a ratio of the flow rate of air divided by the flow rate of water is greater than 1, and control the analyzer to analyze the permeate stream and determine the concentration of that at least one chemical species in the permeate stream.

The details of one or more examples are set forth in the accompanying drawings and the description below. Other features, objects, and advantages will be apparent from the description and drawings, and from the claims.

DETAILED DESCRIPTION

In general, this disclosure describes systems and techniques for operating a membrane separation system by utilizing a feed stream that is predominantly gas and contains a lesser amount of the liquid to be filtered. Where the liquid to be filtered is an aqueous stream and the gas source is air, the feed stream may be referred to as a water-in-air stream to indicate that the aqueous portion of the feed stream is present in a lesser amount than the gaseous portion of the feed stream. In some implementations, the water-in-air stream may be continuously supplied to the membrane system such that any liquid filtered using the membrane system is supplied as part of a feed stream that contains a greater amount of air that liquid. In other implementations, the water-in-air stream may be intermittently supplied to the membrane system such that the membrane system filters a feed stream containing only the liquid or the liquid with a lesser amount of air (e.g., such that there is more liquid than air present in the feed stream) between periods when an water-in-air stream is supplied to the membrane system. In either case, the water-in-air stream supplied to the membrane system can help provide exceptional fouling control, minimizing the amount of fouling on the membrane and increasing the performance of the membrane separation system.

The fouling control benefits associated with using a water-in-air stream are particularly observed in closed membrane system in which a membrane is enclosed within a housing that pressure isolates the membrane from ambient environment. These closed membrane systems, which may also be referred to as housed membrane systems, generally operate by supplying a feed stream to a pressure vessel containing one or more membrane elements. As a result, the entire volume of liquid and air entering housing containing the membrane element contacts the surface of the membrane elements inside of the housing.

Closed membrane systems are generally distinguishable from a second type of membrane system, referred to as a submerged membrane system. In a typical submerged membrane system, one or more membrane elements are submerged in feed water and aeration is preformed underneath the membrane elements. This creates a two-phase turbulence under the membrane elements. This configuration is commonly used in membrane bioreactor (MBR) processes for treating wastewaters. However, in a submerged membrane system, the feed liquid and membrane elements are typically at atmospheric pressure with aeration bypassing the membrane elements. As a result, much of the air supplied underneath the membrane elements passes around the membrane elements without contacting the surface of the membrane elements or having a material impact on the fouling of the membrane element.

Figure 1:
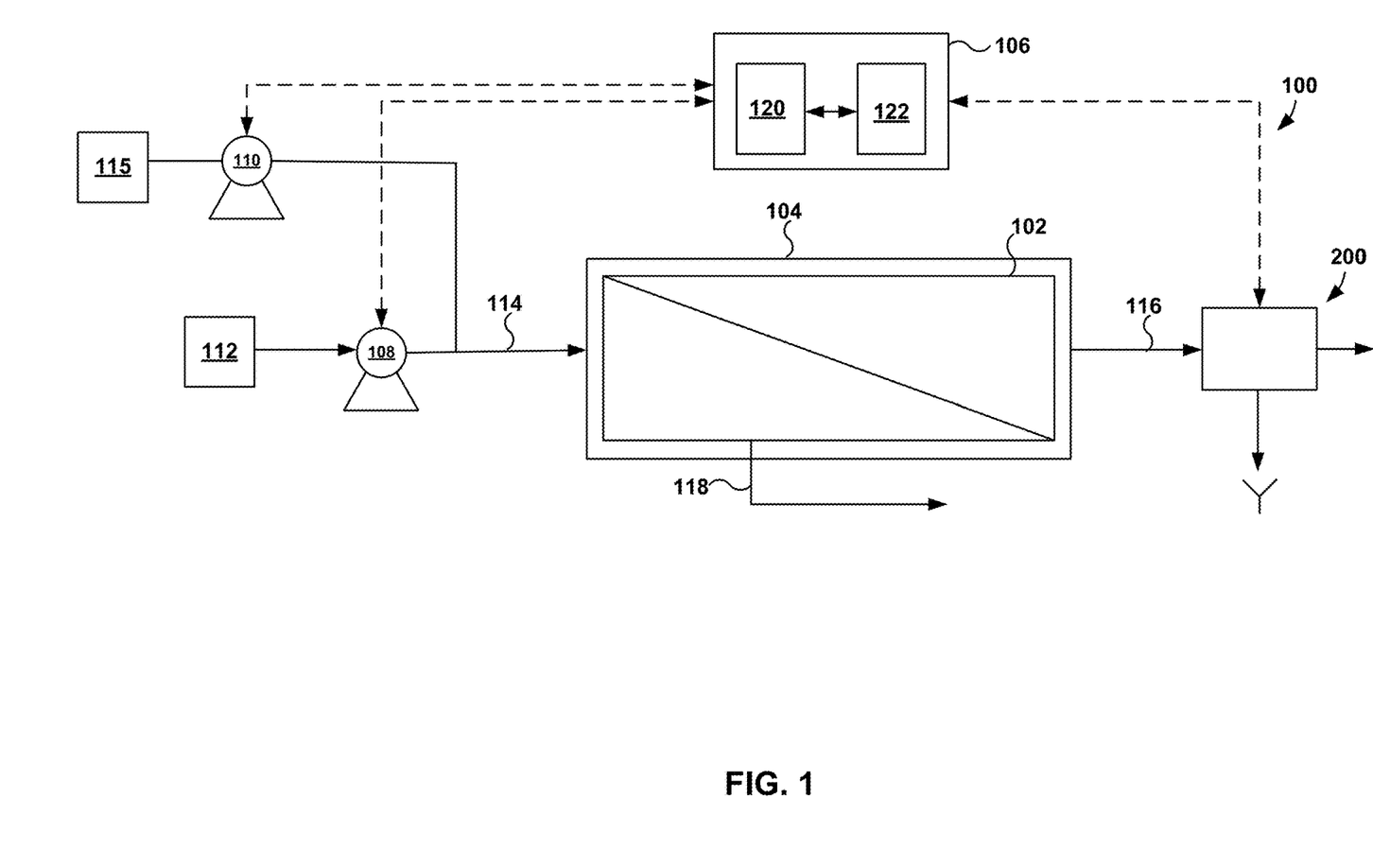
FIG. 1 is a conceptual diagram illustrating an example membrane separation system that receives a water-in-air feed stream containing a greater volume of air than water at least periodically during operation.

FIG. 1 is a conceptual diagram illustrating an example membrane separation system 100 according to the disclosure that receives a water-in-air feed stream containing a greater volume of air than water at least periodically during operation. In the specific example of FIG. 1, membrane separation system 100 is implemented as a pre-filtration step for a downstream automated water analysis system 200. In other examples, membrane separation system 100 may process a feed stream to produce a filtered stream for downstream uses other than for analysis by water analysis system 200.

In the example of FIG. 1, system 100 includes a separation membrane 102 contained within a housing 104. Housing 104 pressure isolates membrane 102 from an ambient environment, e.g., such that the pressure inside of the housing is higher or lower than ambient pressure surrounding the housing. System 100 in the illustrated example also includes a controller 106, a water metering device 108, and an air metering device 110. Water metering device 108 is in fluid communication with a source 112 of water to be purified using membrane 102. Air metering device 110 is in fluid communication with a source of air 115 to combine with water from source 112 to supply a feed stream 114 containing a greater volume of air than water to housing 104 and membrane 102 contained therein. In operation, feed stream 114 is supplied to membrane 102, which is capable of treating or purifying the feed stream by dividing the feed stream into at least a first stream and a second stream, such as a permeate stream 116 and a concentrate stream 118 (which may also be referred to as a reject stream).

At least a portion of the purified water generated by membrane system 100 is supplied to downstream automated water analysis system 200 in the example arrangement of FIG. 1. Operating under the control of controller 106 (or a separate controller from the controller that controls membrane separation system 100), water analysis system 200 can analyze water received from membrane separation system 100 to determine one or more characteristics of the water, such as the concentration of one or more chemical species in the water. This information can then be used to control one or more aspects of the water source 112, such as the addition of one or more chemical agents selected to control the chemical species measured by the water analysis system.

One or more controllers 106 (which is illustrated as a single controller) can be communicatively coupled to various components within membrane separation system 100 and water analysis system 200 to manage the overall operations of the system. For example, controller 106 may be communicatively connected to water metering device 108, air metering device 110, water analysis system 200, and optionally any other controllable components or sensors that may be desirably implemented in system 100 and/or system 200. Controller 106 includes processor 120 and memory 122. Controller 106 communicates with controllable components via connections. For example, signals generated by water analysis system 200 may be communicated to controller 106 via a wired or wireless connection, which in the example of FIG. 1 is illustrated as wired connection. Memory 122 stores software for running controller 106 and may also store data generated or received by processor 120. Processor 120 runs software stored in memory 122 to manage the operation of system 100 and/or system 200.

As described in greater detail below, controller 106 can control water metering device 108 and air metering device 110 to generate feed stream 114 supplied to membrane 102. Controller 106 can control water metering device 108 and air metering device 110 so that the amount of air in feed stream 114 is greater than the amount of water in the feed stream for at least a portion of the time the water is supplied to membrane 102 from source 112. Controller 106 can control water metering device 108 and air metering device 110 to supply feed stream 114 to membrane 102 and generate permeate stream 116 in response to a request from water analysis system 200 calling for water to facilitate analysis by the water analysis system. While various components are described as being controlled by controller 106, in other implementations, some or all of the components may be manually controlled by an operator in the course of performing a technique according to the disclosure.

During operation of system 100, membrane 102 can be contacted with fluid to be purified from source 112 to remove ion, molecules, pathogens, and/or other particulate contaminants. For example, feed stream 114 can contain various solutes, such as dissolved organics, dissolved inorganics, dissolved solids, suspended solids, the like or combinations thereof. Upon separation of feed stream 114 into permeate stream 116 and concentrate stream 118, in membrane 102, the permeate stream can contain a substantially lower concentration of dissolved and/or suspended solutes as compared to the feed stream. On the other hand, the concentrate stream 118 can have a higher concentration of dissolved and/or suspended solutes as compared to the feed stream. In this regard, the permeate stream 116 represents a purified feed stream, such as a purified aqueous feed stream.

System 100 and membrane 102 can be configured for any desired type of membrane separation process, including cross flow separation processes, dead-end flow separation processes, reverse osmosis, ultrafiltration, microfiltration, nanofiltration, electrodialysis, electrodeionization, pervaporation, membrane extraction, membrane distillation, membrane stripping, membrane aeration and the like or combinations thereof. Typically, however, system 100 and membrane 102 may be implemented as a reverse osmosis, ultrafiltration, microfiltration, or nanofiltration membrane separation process.

In reverse osmosis, feed stream 114 is typically processed under cross flow conditions. When so configured, feed stream 114 may flow substantially parallel to the membrane surface such that only a portion of the feed stream diffuses through the membrane as permeate. The cross flow rate is typically high in order to provide a scouring action that lessens membrane surface fouling. This can also decrease concentration polarization effects (e.g., concentration of solutes in the reduced-turbulence boundary layer at the membrane surface, which can increase the osmotic pressure at the membrane and thus can reduce permeate flow). The concentration polarization effects can inhibit the feed stream water from passing through the membrane as permeate, thus decreasing the recovery ratio, e.g., the ratio of permeate to applied feed stream. A recycle loop(s) may be employed to maintain a high flow rate across the membrane surface.

System 100 can employ a variety of different types of membranes as membrane 102. Such commercial membrane element types include, without limitation, hollow fiber membrane elements, tubular membrane elements, spiral-wound membrane elements, plate and frame membrane elements, and the like. For example, reverse osmosis typically uses spiral wound elements or modules, which are constructed by winding layers of semi-porous membranes with feed spacers and permeate water carriers around a central perforated permeate collection tube. Typically, the modules are sealed with tape and/or fiberglass over-wrap. The resulting construction may have one channel that can receive an inlet flow. The inlet stream flows longitudinally along the membrane module and exits the other end as a concentrate stream. Within the module, water can pass through the semi-porous membrane and is trapped in a permeate channel, which flows to a central collection tube. From this tube it can flow out of a designated channel and is collected.

In different applications, membrane 102 can be implemented using a single membrane element or multiple membrane elements depending on the application. For example, multiple membrane elements may be used forming membrane modules that are stacked together, end to end, with inter-connectors joining the permeate tubes of the first module to the permeate tube of the second module, and so on. These membrane module stacks can be housed in one or more housings 104. Within one or more housings 104, feed stream 114 can pass into the first module in the stack, which removes a portion of the water as permeate water. The concentrate stream from the first membrane can then become the feed stream of the second membrane and so on down the stack. The permeate streams from all of the membranes in the stack can be collected in the joined permeate tubes. In these applications, the permeate streams from the different housings or stacks may be combined to form a combined permeate stream 116.

Within most reverse osmosis systems, pressure vessels (e.g., housing 104) may be arranged in either "stages" or "passes." In a staged membrane system, the combined concentrate streams from a bank of pressure vessels can be directed to a second bank of pressure vessels where they become the feed stream for the second stage. Commonly, systems have two to three stages with successively fewer pressure vessels in each stage. For example, a system may contain four pressure vessels in a first stage, the concentrate streams of which feed two pressure vessels in a second stage, the concentrate streams of which in turn feeds one pressure vessel in the third stage. This is designated as a "4:2:1" array. In a staged membrane configuration, the combined permeate streams from all pressure vessels in all stages may be collected and used without further membrane treatment. Multi-stage systems are commonly used when large volumes of purified water are required, for example for boiler feed water. The permeate streams from the membrane system may be further purified by ion exchange or other means.

In a multi-pass system, the permeate streams from each bank of pressure vessels are collected and used as the feed to the subsequent banks of pressure vessels. The concentrate streams from all pressure vessels can be combined without further membrane treatment of each individual stream. Multi-pass systems are typically used when very high purity water is required, for example in the microelectronics or pharmaceutical industries. When system 100 is implemented as a reverse osmosis process, one or more membranes 102 may be configured as a multi-stage and/or multi-pass system.

While system 100 and membrane 102 may be implemented as cross-flow filtration process, in other configurations, the system may be arranged for conventional filtration of suspended solids by passing feed stream 114 through a filter media or membrane in a substantially perpendicular direction. This arrangement can create one exit stream (e.g., purified stream 116) during the service cycle. Periodically, the filter may be backwashed by passing a clean fluid in a direction opposite to the feed, generating a backwash effluent containing species that have been retained by the filter. In this arrangement, system 100 may have a feed stream 114, a purified stream 116, and a backwash stream 118. This type of membrane separation is typically referred to as dead-end flow separation and is typically limited to the separation of suspended particles greater than about one micron in size.

Independent of the specific configuration of system 100 and membrane 102, one or more membranes may be contained within housing 104 during operation to pressure isolate the membrane from the ambient environment. In general, housing 104 may be an enclosed pressure vessel that separates an interior of the housing from an exterior environment. As a result, a pressure inside of housing 104 may be different (e.g., higher or lower) than ambient environmental pressure surrounding the exterior of the housing. By positioning membrane 102 inside of housing 104, substantially all air introduced into the housing as part of a water-in-air feed stream may contact the surface of the membrane. For example, at least 90 volume percent of the air introduced into housing 104 may contact the surface the membrane, such as at least 95 volume percent, at least 98 volume percent, at least 99 volume percent, or at least 99.5 volume percent of the air.

In some implementations, housing 104 is implemented as a closed chamber having a feed inlet, a permeate outlet, and a concentrate outlet. Feed stream 114 can enter the closed chamber via the feed inlet. Permeate stream 116 can discharge from the closed chamber via the permeate outlet. Further, concentrate stream 118 can discharge from the closed chamber via the concentrate outlet.

While housing 104 and the various inlets and/or outlets of the housing can be oriented in various ways, in some examples, the components are arranged to facilitate an upward flow of the incoming air-in-water stream against the membrane surface. For example, housing 104 may be oriented vertically with respect to gravity, with the feed inlet positioned adjacent a bottom end of the housing, and the permeate outlet positioned adjacent a top end of the housing.

When so configured, feed stream 114 may enter housing 104 at or adjacent a bottom of the housing, and flow upwardly with respect to gravity through the housing before permeate stream 116 discharges at or adjacent a top of the housing. In other implementations, the housing 104 may be oriented vertically with respect to gravity, with the feed inlet positioned adjacent a top end of the housing and the permeate outlet positioned adjacent a bottom end of the housing.

In general, membrane separation system 100 is configured to establish a transmembrane pressure across membrane 102 that acts as a driving force for generating permeate stream 116 and concentrate stream 118 from feed stream 114. In some implementations, the transmembrane pressure may be generated by applying a suction force downstream of membrane 102 (e.g., on permeate stream 116) that draws feed stream 114 through housing 104 and membrane 102. Additionally or alternatively, the transmembrane pressure may be generated by supplying a pressurized feed stream 114 to housing 104, where the pressure of the feed stream is greater than the downstream pressure of the permeate stream and/or concentrate stream.

The transmembrane pressure can be measured as the pressure difference between the pressure of feed stream 114 in the pressure of permeate stream 116. The target transmembrane operating pressure for membrane separation system 100 may vary, e.g., depending on the characteristics of feed stream 114 and the configuration of the membrane system, such as the number and type of membrane elements 102 in the system. That being said, in some examples, membrane separation system 100 is configured to operate at a transmembrane pressure of at least 1 kPa, such as a transmembrane pressure ranging from 1 kPa to 600 kPa.

When membrane separation system 100 operates at a positive pressure, feed stream 114 may be a pressurized stream the enters housing 104. Water metering device 108 and/or air metering device 110 may pressurized water from water source 112 and air from air source 115, respectively, to generate the pressurized feed stream. Feed stream 114 may be pressurized to a pressure of at least 1 kPa, such that the feed stream contacts membrane 102 inside of housing 104 at a pressure of at least 1 kPa. For example, feed stream 114 may be pressurized to a pressure of at least 2 kPa, such as at least 5 kPa, at least 10 kPa, at least 50 kPa, at least 100 kPa, or at least 250 kPa.

In other examples when membrane separation system 100 operates in a vacuum pressure, one or more suction pumps may be implemented downstream of housing 104 to create a suction pressure that draws feed stream 114 through housing 104 and membrane 102. For example, a suction pump may be connected to permeate stream 116 that creates a vacuum pressure inside of housing 104, drawing feed stream 114 through the housing. The suction pump may generate a suction pressure on the permeate stream of at least 1 kPa, such as a suction pressure of at least 2 kPa or of at least 5 kPa, such as at least 10 kPa, at least 50 kPa, at least 100 kPa, or at least 250 kPa. In these implementations, feed stream 114 entering housing 104 may or may not be pressurized at a positive pressure (e.g., by water metering device 108 and/or air metering device 110).

System 100 can be used to purify any desired type of fluid. Example aqueous (water-based) liquid feed sources 112 that may be purified using system 100 include raw water streams (e.g., extracted from a fresh water source), waste water and recycle water streams (e.g., from municipal and/or industrial sources), streams in food and beverage processes, streams in pharmaceutical processes, streams in electronic manufacturing, streams in utility operations, streams in pulp and paper processes, streams in mining and mineral processes, streams in transportation-related processes, streams in textile processes, streams in plating and metal working processes, streams in laundry and cleaning processes, streams in leather and tanning processes, streams in paint processes, and combinations thereof. For example, a membrane separate process may commonly be deployed for water treatment and the preparation of water such as drinking water, pure water, ultra-pure grade water, process water for electricity, electronic and/or semiconductor industries, process water for the medical field, water for agents, water for injection, aseptic pyrogen-free pure water, process water of food and beverage uses, water for a boiler, and/or water for washing and cooling. A membrane separation processes can also be applied to fields such as the desalination of seawater or brackish water.

In some examples, water source 112 is a boiler water stream. In other examples, water source 112 is a cooling water stream. A cooling water stream may be a stream obtained from a water system that includes a cooling tower that reduces a temperature of a cooling water stream through evaporative cooling. The water system in these examples may also include one or more heat exchanges in which the cooling stream passes on a cold side of the heat exchanger and picks up thermal energy from a comparatively hot process stream passing on a hot side of the heat exchanger.

Independent of the source 112 of water used to generate the water-in-air feed stream 114 supplied to membrane 102, the water may contain various organic and/or inorganic species. In this regard, it should be appreciated that reference to "water" and a "water stream" (e.g., water-in-air stream) in the present disclosure is not intended to exclude the presence of one or more additional chemical species in the water, unless otherwise indicated. Example chemical species that may be present in the water include salts (e.g., calcium, sodium, magnesium), metal component (e.g., iron, aluminum, and/or zinc), phosphates, and/or biological organism. When source 112 includes water containing organic and/or inorganic species, the water molecules ($H_2O$) may constitute greater than 75 weight percent of the water stream, such as greater than 90 weight percent, greater than 95 weight percent, or greater than 98 weight percent.

In some example, a membrane cleaning agent (e.g., biofouling control agent) may be added to water obtained from source 112 prior to contacting membrane 102 with the water. Example cleaning agents that may be used include chlorine, chlorine dioxide, chloramine, bromine (e.g., DBNPA), at the like. In other examples, a membrane cleaning agent is not added to the water obtained from source 112 prior to introduction into housing 104.

As mentioned, controller 106 can control membrane system 100 can generate a water-in-air feed stream 114 containing a greater volume of air than water at least periodically during operation. Controller 106 can generate the feed stream 114 having a greater volume of air than water by supplying a greater volume of air from air source 115 than the volume of water supplied from water source 112 to housing 104 containing membrane 102. Controller 106 may control water metering device 108 and air metering device 110 to control the volumes of water and air, respectively, supplied to housing 104.

In general, controller 106 can generate a water-in-air feed stream by supplying a greater volumetric flow rate of air to housing 104 than the volumetric flow rate of water supplied to the housing. As a result, the ratio of the flow rate of air divided by the flow rate of water may be greater than 1. In some implementations, the volume of air supplied to housing 104 may be significantly greater than the volume of water supplied to the housing, when supplying a water-in-air stream. For example, the ratio of the volumetric flow rate of air delivered to housing 104 divided by the volumetric flow rate of water delivered to the housing may be at least two, such as at least three, at least five, at least 10, at least 20, or at least 25. In some specific implementations, for instance, the ratio may range from about two to about 50, such as about three to about 25, from about three to about 20, or from about four to about 10.

In the example of FIG. 1, water from source 112 and air from source 115 are shown combining together upstream of housing 104 to form a combined water-in-air feed stream 114 that is supplied to housing 104. The water and air streams may be combined together in a number of different ways. For example, the water stream may be injected into the air stream or, alternatively, the air may be injected into the water stream. In some examples, the combined water in air stream may pass through one or more mixing devices (e.g., a static mixer) upstream of housing 104 before entering the housing. In still other examples, the water and air streams may be separately introduced into housing 104 to generate the water-in-air feed stream 114 inside of the housing rather than generating the feed stream outside of the housing and supplying the combined water in air streams to the housing.

In some implementations, a water-in-air stream may be continuously supplied to the membrane system such that any liquid filtered using the membrane system is supplied as part of a feed stream that contains a greater amount of air that liquid. In these implementations, feed stream 114 supplied to membrane 102 may always have a greater amount of air than water. In other implementations, a water-in-air stream may be intermittently supplied to the membrane system. In this implementations, the feed stream supplied to membrane 102 may vary between being a water-in-air stream (containing a greater amount of air than water) and a water stream (e.g., containing only water from source 112, or containing a lesser amount of air than water).

When membrane separation system 100 operates to intermittently supply the water-in-air stream to membrane 102, controller 106 may intermittently terminate the supply of air from source 115 (e.g., by controlling air metering device 110). Membrane separation system 100 may be operated to intermittently supply the water-in-air stream to membrane 102, e.g., with a liquid only or predominately liquid stream being supplied to the membrane between when the water-in-air stream is supplied to membrane. This can reduce air demands and associated energy operating costs for the membrane separation system.

In implementations when membrane separation system 100 operates to intermittently supply the water-in-air stream to membrane 102, a minimum amount of water supplied from source 112 and contacted the membrane may be supplied as part of the water-in-air stream. For example, at least 5 volume percent of the water supplied from source 112 and processed by membrane 102 may be supplied as part of the water-in-air stream, such as at least 10 vol %, at least 30 vol %, at least 50 vol %, or at least 75 vol %. The remaining volume of water from source 112 that is introduced into housing 104 to contact membrane 102 may be supplied as part of feed stream 114 that is devoid of added air and/or that is part of the feed stream that contains a greater volume of water than air.

In the example of FIG. 1, at least a portion of permeate stream 116 generated by membrane separation system 100 is applied to automated water analysis system 200. Automated water analysis system 200 can analyze the water to determine one or more characteristics of the water, such as temperature, pH, conductivity, and/or a concentration of one or more chemical species of interest in the water. In some examples, the information generated by automated water analysis system 200 concerning the concentration of one or more chemical species of interest can be used as a process control variable for controlling the source of water 112. For example, the information may be used to control addition of one or more chemical agents selected to control the chemical species of interest (e.g., via precipitation or by binding to the chemically species).

Figure 2:
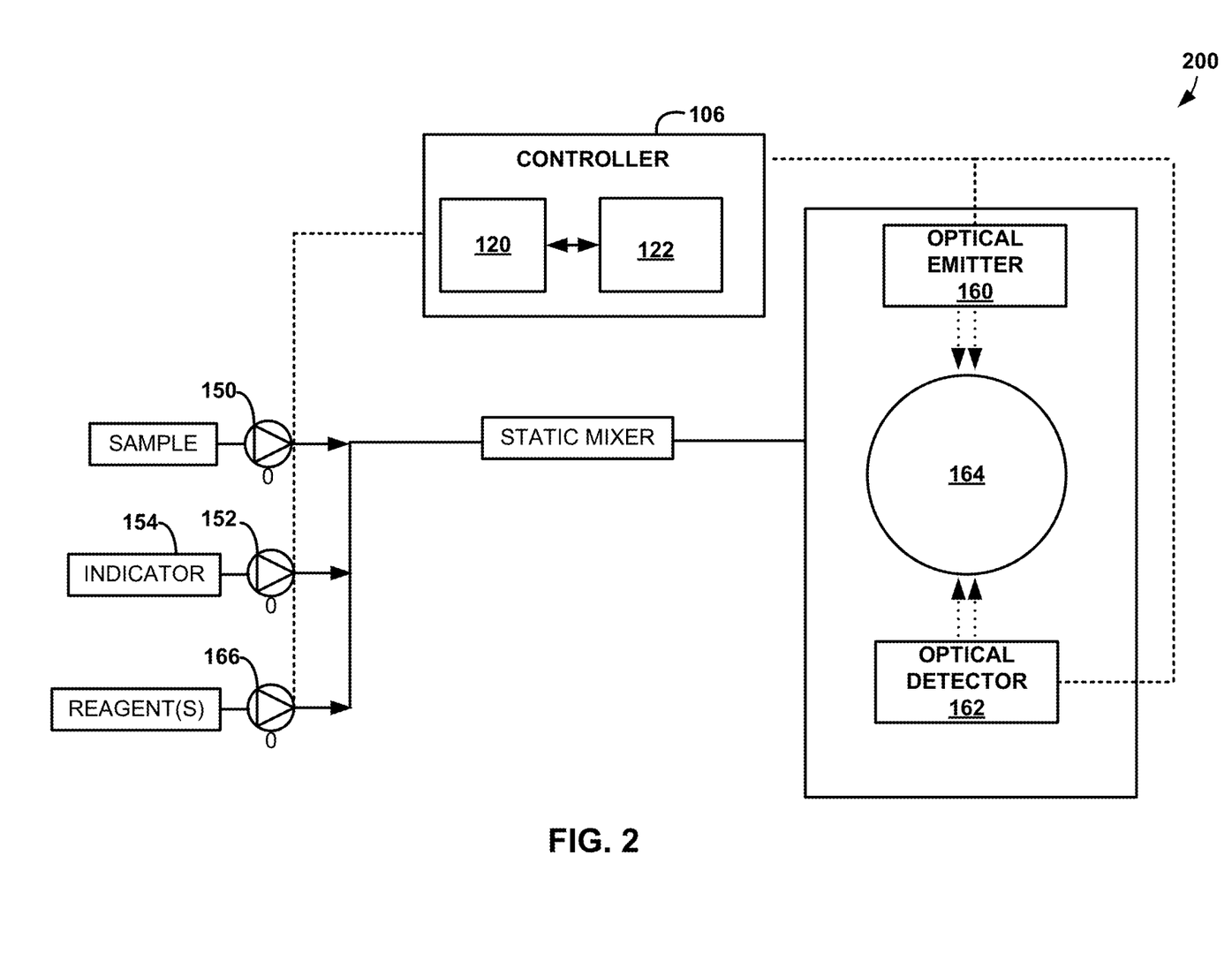
FIG. 2 is a block diagram illustrating one example configuration of an automated water analysis system that can be used to analyze water received from the membrane separation system of FIG. 1.

FIG. 2 is a block diagram illustrating one example configuration of an automated water analysis system 200 that can be used to analyze water received from membrane separation system 100. In particular, FIG. 2 illustrates water analysis system 200 implemented as an optical sensor that can be used to measure a colorimetric response between a chemical species of interest in the water and an indicator, thereby providing an indication of the concentration of the chemical species of interest. As illustrated, the analysis system includes an optical emitter and an optical detector as well as hardware for extracting a water sample and mixing one or more reagents with the sample prior to optical analysis. In other configurations, water analysis system 200 may be implemented without the reagent and mixing features of FIG. 2 or may have other configurations than the specific example illustrated.

Moreover, water analysis system 200 in FIG. 2 is illustrated as being controlled by controller 106 discussed above with respect to FIG. 1. Controller 106 can be communicatively connected to the controllable components within water analysis system 200 to send and/or receive data and control signals to/from the components. However, the functions described as being performed by controller 106 in FIG. 2 may be performed by a different system controller, one or more remote computing devices, and/or other controller hardware and/or software.

In the example of FIG. 2, water analysis system 200 is illustrated as including a sample pump 150 that can operate to provide a sample containing an unknown concentration of a chemical species of interest in permeate stream 116. Sample pump 150 can extract a sample of water from a fluid pathway through which permeate stream 116 flows for analysis. In other examples, permeate stream 116 may be supplied under pressure to water analysis system 200, e.g., without requiring sample pump 150.

Water analysis system 200 can also include an indicator pump 152 that pumps indicator from a source of indicator 154 (e.g., reservoir or container containing indicator) for mixing with the sample of water for subsequent optical analysis. The indicator can complex or otherwise react with one or more chemical species of interest in the water sample to produce a measurable optical response, the extent of which varies in response to the amount of the chemical species present in the sample under analysis. The number and type(s) of indicator combined with the water sample may be selected by the number and type(s) of chemical species of interest for measurement in the water sample. Example chemical species that may be measured include organic and/or inorganic species, such as calcium, sodium phosphate, iron, and/or other species of interest.

To measure the optical response of the sample containing the chemical species-indicator reaction product (e.g., a calcium-indicator complex or phosphate-indicator complex), water analysis system 200 may include one or more optical emitters 160 and one or more optical detectors 162 optically connected to a sample receiving space 164 for optical analysis. Sample receiving space 164 may be an optical cell that receives and holds a static portion of fluid that undergo optical analysis, for example, in a stop flow configuration with the sample subsequently being discharged. As another example, sample receiving space 164 may be or include a fluid conduit through which a flowing stream of fluid passes with optical analysis being performed on the flowing stream of fluid.

Reaction between the one or more indicators introduced into the sample and one or more of the chemical species of unknown concentration in the sample can produce an optically detectable change. The concentration of chemical species of interest can be proportional to the measured optical response of the sample. For example, the optical response may be a colorimetric change that occurs through when a complex is formed between chemical species of interest in the sample and the indicator. The reaction between the indicator and chemical species of interest may occur in or upstream of sample receiving space 164 and be detected by measuring an absorbance of the sample.

In some examples, water analysis system 200 is configured to introduce one or more additional reagents to a sample undergoing optical analysis. The one or more additional reagents may be present with indicator and introduced simultaneously with the indicator or may be introduced separately from the indicator. In the example of FIG. 2, water analysis system 200 is illustrated as including one or more additional reagent pumps 166 fluidly connected to one or more additional sources of reagent. In other examples, the indicator 154 and other desired reagents may be mixed and/or stored together and delivered through single pump 152 instead of being separately introduced.

Example chemical reagents that may be added to the fluid sample in addition to the indicator include, but are not limited to, a pH adjuster and/or buffer, a reaction catalyst, a sequestrant, a surfactant, a range extender or a combination thereof. For example, controller 106 may control the addition of a pH adjustor to the sample undergoing analysis so the sample is within a pH range where the calcium-indicator complex forms. The specific types of indicators and/or reagents added to the sample will vary depending on the specific application of the system.

Controller 106 can control the operation of optical emitter 160 and receives signals concerning the amount of light and/or frequency or wavelength(s) of light detected by optical detector 162. In some examples, controller 106 processes signals received from optical detector 162 during analysis of a water sample containing an unknown concentration of a chemical species of interest and determines a concentration of chemical species in the sample based on calibration data stored in memory. The calibration curve data may relate light detected by optical detector 162 to a concentration of the chemical species in the fluid under analysis.

As discussed above with respect to FIG. 1, information concerning the concentration of the chemical species of interest can be used as control information for modifying the source of water 112 from which the permeate stream 116 is obtained. Controller 106 (or another controller) may be configured to take a variety of control actions based on the measured concentration of one or more chemical species of interest.

In some examples, controller 106 may control addition of a chemical agent to water source 112 selected to counteract the chemical species of interest and/or fouling attributable to the chemical species of interest. For example, controller 106 may control addition of a scale inhibitor and/or pH control agent to inhibit scale fouling, control addition of a corrosion inhibitor and/or pH control agent to inhibit corrosion fouling, and/or may control addition of a biocide and/or biodispersant to inhibit biofouling. Example chemical agents that may be added to water source 112 include, but are not limited to, polymers (dispersants and scale inhibitors), organophosphorus compounds such as phosphinosuccinic oligomer (PSO, scale and corrosion inhibitor), zinc (corrosion inhibitor), orthophosphate (corrosion inhibitor), polyphosphates (scale and corrosion inhibitors), biocides, and combinations thereof. Where the chemical agent is selected to counteract a chemical species of interest (e.g. calcium, phosphate), the chemical agent may be referred to as a control agent for the chemical species (e.g., a calcium control agent, a phosphate control agent). Additionally or alternatively, one or more chemical agents may be added into the water to adjust the pH of the water. Examples of pH adjusting control agents include mineral acids, organic acids, and inorganic bases.

Controller 106 may control the addition of one or more chemical agents to source 112 based on the measured concentration of the chemical species of interest by starting a dosing pump or increasing an operating rate of the pump based on the measured concentration of the chemical species of interest (e.g., the measured concentration equaling or exceeding one or more concentration thresholds). Additionally or alternatively, controller 106 may stop the dosing pump or decrease an operating rate of the pump based on the measured concentration of the chemical species of interest (e.g., the measured concentration falling below one or more concentration thresholds).

Features described as fluid metering devices in membrane separation system 100 (e.g., water metering device 108, air metering device 110), may be any device that controls delivery of fluid to generate feed stream 114 for supply to housing 104. For example, each metering device may be a pumping mechanism that receives fluid on a draw side, pressurizes, the fluid, and discharges the pressurized fluid at an increased pressure. Example pumps may comprise a peristaltic pump or other form of continuous pump, a positive-displacement pump, an air compressor, or any other type of pump appropriate for the particular application. Additionally or alternatively, one or more metering devices may be implemented as a valve or other fluid control device (e.g., when fluid from water source 112 and/or air source 115 is already pressurized or is drawn through housing 104 by a suction pump positioned downstream of the housing).

The source of air 115 may be ambient air that is drawn into a compressor or other pumping device for supply to housing 104. Alternatively, the source of air 115 may be a reservoir (e.g., tank) that stores pressurized gas for delivery to housing 104. While membrane separation system 100 is generally described as using air (e.g. approximately 78% nitrogen, approximately 21% oxygen, and approximately 1% argon), the system may operate with other gases without departing from the scope of the disclosure. Example gases that may be used include nitrogen, carbon dioxide, oxygen, and the like.

In the example of FIG. 1, permeate stream 116 generated by membrane separation system 100 is supplied to automated water analysis device 200. This configuration may be useful to implement an online automated water analysis system that can operate without user intervention for an extended period of time (e.g., at least two weeks, at least one month, at least two months, at least six months, at least one year). By operating membrane separation system 100 with a water-in-air feed stream as described herein, the water-in-air feed stream may reduce or eliminate fouling on membrane 102 during extended service. This can allow the system to operate for an extended period of time without necessitating user intervention. In these applications, membrane separation system 100 may be a comparatively small-sized system generating a comparatively small permeate stream for downstream analysis, such as a system generating less than 100 Liters/min, such as less than 10 L/min, less than 5 L/min, less than 2 L/min, less than 1 L/min, or less than 0.5 L/min.

In other implementations, the systems and techniques of the present disclosure may be used to generate a permeate stream 116 intended for downstream applications other than analysis by an automated water analysis device. For example, permeate stream 116 may be used personal consumption, industrial processes, and/or any other desired application. In these implementations, the volume of water processed by membrane separation system 100 may be greater than in a comparatively smaller system feeding automated water analysis device 200. As a result, the amount of air needed to generate the water-in-air feed stream may be particularly large. The increased energy costs associated with supplying air to these larger scale applications may limit deployment to select applications, but this does not impact the technical feasibility of the applications.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a non-transitory computer-readable storage medium, containing instructions. Instructions embedded or encoded in a computer-readable storage medium may cause a programmable processor, or other processor, to perform the method, e.g., when the instructions are executed. Non-transitory computer readable storage media may include volatile and/or non-volatile memory forms including, e.g., random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

The following examples may provide additional details about membrane separation systems and the anti-fouling efficacy of a water-in-air feed stream according to the disclosure.

Example: Comparison Between Water-In-Air and Air-In-Water Feed Streams

An example was performed to study the effect of operating a membrane separation system using a water-in-air feed stream (containing a greater volume of air than water) compared to operating using an air-in-water feed stream (containing a greater volume of water than air). The feed streams were prepared by obtaining water from an operating cooling water tower. The feed water had an unspecified quantity of organic and inorganic colloids.

Two different membrane modules were used to study the water-in-air and air-in-water feed streams. The first module used to study the water-in-air feed stream was a comparatively small membrane module having an inner diameter of 12 mm. The second module used to study the air-in-water feed stream was a comparatively large membrane module having an inner diameter of 25 mm. Both modules were operated under constant pressure mode by maintaining a constant transmembrane pressure of approximately 5 kPa. Table 1 shows the operating conditions for the two membrane modules supplied with water-in-air and air-in-water feed streams, respectively.

TABLE 1

Operating conditions for experimental membrane modules.

| | Water-in-Air feed stream | Air-in-Water feed stream |
|---|---|---|
| Membrane Surface Area (cm$^2$) | 335 | 1,000 |
| Air Flow (L/min) | 1-2 | ~0.5 |
| Water flow (L/min) | ~0.18 | 0.5-1.0 |
| Trans-membrane pressure (kPa) | 5-10 | 5-10 |
| Membrane module ID (mm) | 12 | 25 |

Because the membrane module supplied with the water-in-air feed stream has one third the surface area of the membrane module suppled with the air-in-water feed stream, it was expected that the module supplied with the air-in-water feed stream would produce more permeate. In fact, the membrane module supplied with the water-in-air feed stream produced much more permeate.

Figure 3:
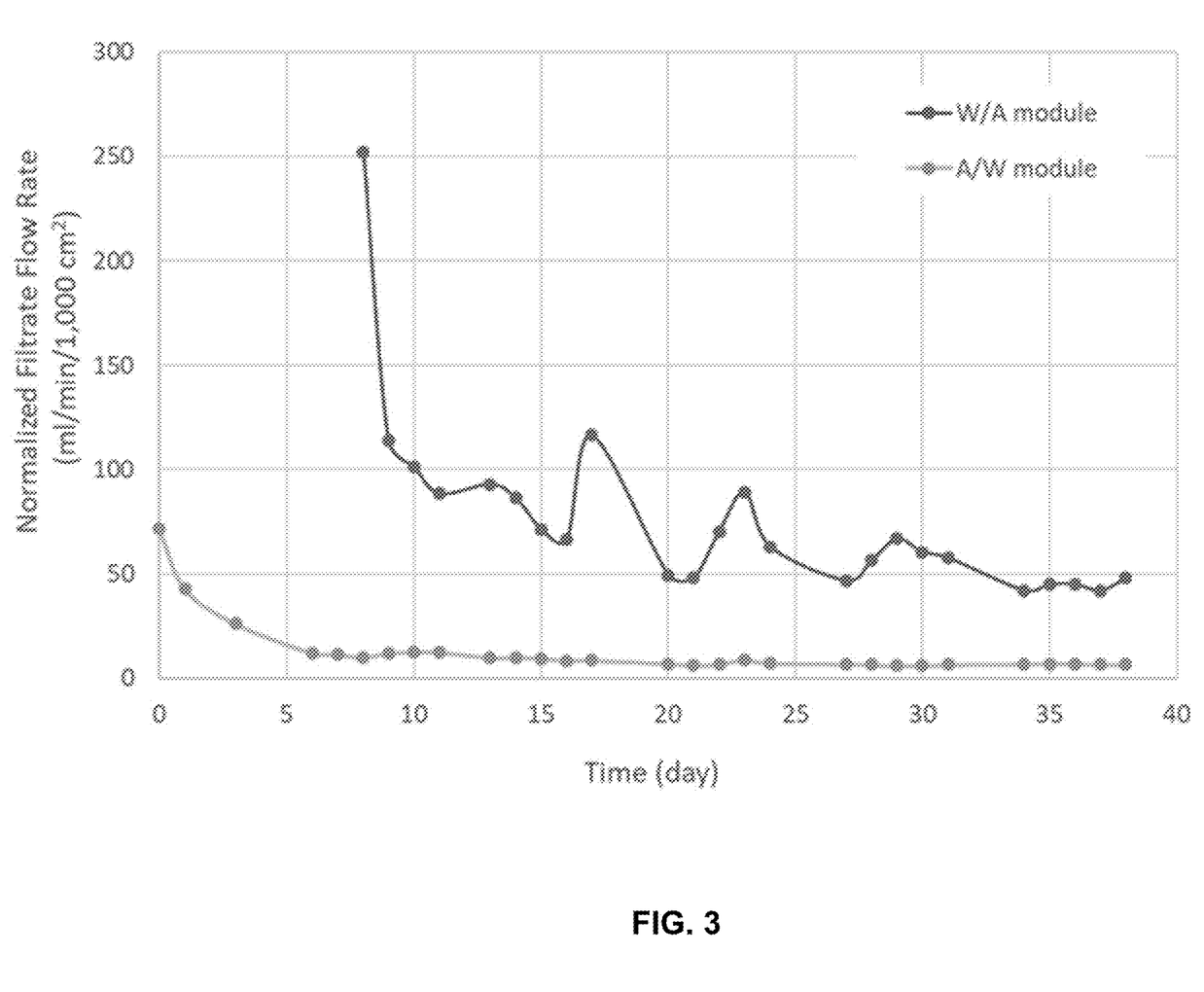
FIG. 3 is plot showing normalized permeate flow rate versus time using a water-in-air feed stream compared to an air-in-water feed stream.

The permeate flow rates produced from the two membrane modules were normalized against membrane surface areas to allow more accurate comparison. FIG. 3 is plot showing normalized permeate flow rate versus time using a water-in-air feed stream compared to an air-in-water feed stream. The data show that the water-in-air feed stream performs an average of 8 times better than the air-in-water feed stream under the same operating conditions.

The invention claimed is:

1. A method of controlling pre-filtration fouling in an automated water analysis system, the method comprising:
   generating a feed stream by combining a flow rate of air with a flow rate of water, wherein a ratio of the flow rate of air divided by the flow rate of water is greater than 1;
   contacting a membrane with the feed stream inside of a housing, thereby generating a permeate stream and a concentrate stream, wherein the housing pressure isolates the membrane from an ambient environment; and
   analyzing the permeate stream to determine a concentration of at least one chemical species in the permeate stream.

2. The method of claim 1, wherein the ratio of the flow rate of air divided by the flow rate of water is a value within a range from about 3 to about 20.

3. The method of claim 1, wherein the flow rate of water is supplied from a cooling water stream.

4. The method of claim 1, wherein analyzing the permeate stream to determine the concentration of at least one chemical species in the permeate stream comprises introducing a colorimetric reagent to a sample of the permeate stream to form an optical analysis solution and optically analyzing the optical analysis solution.

5. The method of claim 1, wherein the at least one chemical species comprises calcium.

6. The method of claim 5, further comprising controlling addition of a calcium control agent into a water system from which the water stream is obtained based on a determined calcium concentration.

7. The method of claim 1, wherein contacting the membrane with the feed stream inside of the housing comprises contacting the membrane with the feed stream at a trans-membrane pressure ranging from 1 kPa to 600 kPa, the trans-membrane pressure being a pressure difference between a pressure of the feed stream and a pressure of the permeate stream.

8. The method of claim 1, wherein the housing comprises a tubular chamber having a feed inlet, a permeate outlet, and a concentrate outlet, and the housing is oriented vertically with respect to gravity, the feed inlet is positioned adjacent a bottom end of the housing, and the permeate outlet is positioned adjacent a top end of the housing.

9. The method of claim 1, wherein contacting the membrane with the feed stream comprising the flow rate of air combined with the flow rate of water comprises continuously contacting membrane with the feed stream comprising the flow rate of air combined with the flow rate of water.

10. The method of claim 1, further comprising intermittently terminating the flow rate of air and contacting the membrane with the flow rate of water without the flow rate of air to generate the permeate stream and the concentrate stream.

11. The method of claim 10, wherein at least 10% of the flow rate of water contacting the membrane is combined with the flow rate of air to generate the feed stream prior to contacting the membrane.

12. The method of claim 1, wherein the membrane is selected from the group consisting of a microfiltration membrane, an ultrafiltration membrane, a nanofiltration membrane, and a reverse osmosis membrane.

13. A method of controlling membrane fouling comprising:
   generating a feed stream by combining a flow rate of air with a flow rate of water, wherein a ratio of the flow rate of air divided by the flow rate of water is greater than 1; and
   contacting a membrane with the feed stream inside of a housing, thereby generating a permeate stream and a concentrate stream, wherein the housing pressure isolates the membrane from an ambient environment.

14. The method of claim 13, wherein the ratio of the flow rate of air divided by the flow rate of water is a value within a range from about 3 to about 20.

15. The method of claim 13, wherein the flow rate of water is supplied from a cooling water stream.

16. The method of claim 13, wherein contacting the membrane with the feed stream inside of the housing comprises contacting the membrane with the feed stream at a trans-membrane pressure ranging from 1 kPa to 600 kPa, the trans-membrane pressure being a pressure difference between a pressure of the feed stream and a pressure of the permeate stream.

17. The method of claim 13, further comprising analyzing the permeate stream to determine a concentration of at least one chemical species in the permeate stream.

18. The method of claim 17, wherein analyzing the permeate stream to determine the concentration of at least chemical species in the permeate stream comprises introducing a colorimetric reagent to a sample of the permeate stream to form an optical analysis solution and optically analyzing the optical analysis solution, and further comprising controlling addition of a chemical species control agent into a water system from which the water stream is obtained based on a determined chemical species concentration.

19. The method of claim 18, wherein the at least chemical species comprises calcium.

20. A system comprising:
a membrane positioned in a housing that pressure isolates the membrane from an ambient environment, the membrane being configured to separate a feed stream into a permeate stream and a concentrate stream;
a water metering device configured to provide a flow rate of water;
an air metering device configured to provide a flow rate of air that combines with the flow rate of water to generate the feed stream supplied to the housing;
an analyzer positioned to measure a concentration of at least one chemical species in the permeate stream; and
a controller communicatively coupled to the water metering device, the air metering device, and the analyzer, wherein the controller is configured to:
control the water metering device and the air metering device to generate the feed stream with a ratio of the flow rate of air divided by the flow rate of water is greater than 1, and
control the analyzer to analyze the permeate stream and determine the concentration of that at least one chemical species in the permeate stream.

* * * * *